US010287242B2

(12) United States Patent
Mehta et al.

(10) Patent No.: US 10,287,242 B2
(45) Date of Patent: May 14, 2019

(54) PROCESS FOR THE SYNTHESIS OF HIGHLY PURE CATIONIC SURFACTANT PRODUCTS

(75) Inventors: Dilip S. Mehta, Mumbai (IN); Mayank Shastri, Vadodara (IN)

(73) Assignee: ORGANISTRY, LLC, Fairfield, NJ (US)

( * ) Notice: Subject to any disclaimer, the term of this patent is extended or adjusted under 35 U.S.C. 154(b) by 0 days.

(21) Appl. No.: 14/369,410

(22) PCT Filed: May 4, 2012

(86) PCT No.: PCT/IB2012/052238
§ 371 (c)(1),
(2), (4) Date: Jun. 27, 2014

(87) PCT Pub. No.: WO2013/098659
PCT Pub. Date: Jul. 4, 2013

(65) Prior Publication Data
US 2014/0323756 A1    Oct. 30, 2014

(30) Foreign Application Priority Data

Dec. 28, 2011 (IN) .......................... 3684/MUM/2011

(51) Int. Cl.
*C07C 229/00* (2006.01)
*C07C 277/08* (2006.01)

(52) U.S. Cl.
CPC .................................. *C07C 277/08* (2013.01)

(58) Field of Classification Search
CPC .......................... C07C 277/08; C07C 279/14
See application file for complete search history.

(56) References Cited

U.S. PATENT DOCUMENTS

| | | | | |
|---|---|---|---|---|
| 3,049,537 A | * | 8/1962 | Klug | C08B 11/08 536/89 |
| 3,296,260 A | | 1/1967 | Knoth, Jr. | |
| 3,499,893 A | * | 3/1970 | Crast, Jr. | C07D 501/20 540/216 |
| 3,985,722 A | | 10/1976 | Yoshida et al. | |
| 5,071,960 A | | 12/1991 | Turowski et al. | |
| 5,387,697 A | * | 2/1995 | Hen | 548/533 |
| 5,501,839 A | * | 3/1996 | Tarantino | B01L 99/00 422/547 |
| 5,780,658 A | | 7/1998 | Martinez-Pardo et al. | |
| 8,278,478 B2 | | 10/2012 | Ghare | |
| 2010/0016258 A1 | | 1/2010 | Lynch | |
| 2010/0152480 A1 | * | 6/2010 | Sadhu | C07C 231/02 560/169 |
| 2011/0077423 A1 | * | 3/2011 | Ghare | C07C 277/08 560/169 |

FOREIGN PATENT DOCUMENTS

| | | |
|---|---|---|
| EP | 0 749 960 B1 2001 | 6/2001 |
| EP | 1 294 678 B1 2006 | 3/2006 |
| WO | WO2010/117258 | * 10/2010 |
| WO | WO 2010/117258 | 10/2010 |

OTHER PUBLICATIONS

Chattopadhyay (Brine-Mediated Efficient Benzoylation of Primary Amines and Amino Acids, Synthetic Communications, 38: 4068-4075, published 2008, as cited in IDS filed Nov. 28, 2016).*
'RNR (Review on N-acylation reaction, p. 1-33, published 2007) (Year: 2007).*
Bakal G, Diaz A; "The Lowdown on Lauric Arginate"; Food Quality magazine, 2005.
Barroso JM: "Directive 76/768/EEC concerning cosmetic products"; Official Journal of the European Union 2010.
JECFA: Ethyl Lauroyl Arginate FAO JECFA Monographs 7, 2009.
Lakshmanan AR, Prasad MVR, Ponraju D, Krishnan H: "A novel method of non-violent dissolution of sodium metal in a concentrated aqueous solution of Epsom salt." Journal of Solid State Chemistry 2004, 177(10):3460-3468.
Halpern M: Hydroxide ion initiated reactions under phase-transfer-catalysis conditions.5. Isomerization of allylbenzene via hydroxide ion extraction. The Journal of Organic Chemistry 1983, 48(7):1022-1025.
Mehta D, Mehta P: "pH Facts & Fallacies", Chemical Industry Digest 2006:53-57.
Wehtje, et al., "Continuous control of water activity during biocatalysi in Organic Media" Biotechnolgy Techniques, 7(12), 873-878 (Dec. 1993).
International Search Report and Written Opinion of the International Searching Authority, for PCT/IB2012/052238, issued Sep. 5, 2012.
Pal et al: "Molecular mechanism of physical gelation of hydrocarbons by fatty acid amides of natural amino acids", Tetrahedron, Elsevier Science Publishers, Amsterdam, NL, vol. 63, No. 31, Jun. 21, 2007 (Jun. 21, 2007), pp. 7334-7348, XP022124599, ISSN: 0040-4020, DOI: 10.1016/J.TET.2007.05.028.

(Continued)

*Primary Examiner* — Yevegeny Valenrod
*Assistant Examiner* — Blaine G Doletski
(74) *Attorney, Agent, or Firm* — Bryan D. Zerhusen, Esq.; Cantor Colburn LLP

(57) ABSTRACT

The present invention is related to synthesis of highly pure cationic surfactant products by eliminating or reducing impurities generation that has beset prior art. This is achieved through the N-acylation of ester of amino acid and its inorganic salts or its organic salts (e.g. amino acid or hydrochloride of amino acid or sulfate of amino acid or acetate of amino acid etc.) in non-hydrolytic or nearly non-hydrolytic reaction conditions involving mono or biphasic reaction system with fatty acid halide ($C_4$ to $C_{20}$), under moderate uniform basic condition yielding high purity N-acyl substituted amino acid ester, particularly ethyl lauroyl arginate. The present process achieves pH control through process strategy rather than the measurement and control steps. This ambient temperature process is stable through a range of temperature variation eliminating rigid low temperature control.

2 Claims, No Drawings

(56) References Cited

OTHER PUBLICATIONS

Nizal S. Chandrakumar et al: "Synthesis of enzyme-inhibitory phospholipid analogs II. Preparation of chiral 1-acyl-2-acylamido-2-deoxyglycerophosphorycholines from serine", Tetrahedron Letters, vol. 22, No. 31, Jan. 1, 1981 (Jan. 1, 1981), pp. 2949-2952, XP055196988, ISSN: 0040-4039, DOI: 10.1016/S0040-4039(01)81796-2.

Bhattacharya S et al: "First report of phase selective gelation of oil from oil/water mixtures. Possible implications toward containing oil spills", Chemical CommunicationsChemical Communications—ChemCom; [6015D], Royal Society of Chemistry, GB, No. 2, Jan. 21, 2001 (Jan. 21, 2001), pp. 185-186, XP002220131, ISSN: 1359-7345, DOI: 10.1039/B0078480.

Samir Ghosh et al: "A short and efficient synthesis of valsartan via a Negishi reaction", Beilstein Journal of Organic Chemistry, vol. 6, Jan. 1, 2010 (Jan. 1, 2010), XP055008398, ISSN: 1860-5397, DOI: 10.3762/bjoc.6.27.

East J E et al: "Synthesis and structure-activity relationships of tyrosine-based inhibitors of autotaxin (ATX)", Bioorganic & Medicinal Chemistry Letters, Pergamon, Amsterdam, NL, vol. 20, No. 23, Dec. 1, 2010 (Dec. 1, 2010), pp. 7132-7136, XP027459373, ISSN: 0960-894X, DOI: 10.1016/J.BMCL.2010.09.030 [retrieved on Nov. 2, 2010].

Audrey Martinez et al: "A novel one-pot, two-step synthesis of-acyl-1,3-thiazolidines and-acyl-1,3-oxazolidines as potential double prodrugs of formaldehyde", Tetrahedron Letters, Pergamon, GB, vol. 52, No. 13, Jan. 12, 2011 (Jan. 12, 2011), pp. 1444-1447, XP028153370, ISSN: 0040-4039, DOI: 10.1016/J.Tetlet.2011.01.049 [retrieved on Jan. 18, 2011].

Gautam Chattopadhyay et al: "Brine-Mediated Efficient Benzoylation of Primary Amines and Amino Acids", Synthetic Communications, vol. 38, No. 23, Nov. 3, 2008 (Nov. 3, 2008), pp. 4068-4075, XP055197018, ISSN: 0039-7911, DOI: 10.1080/00397910802250929.

Anonymous: "A guide to pH measurement", , Oct. 1, 2007 (Oct. 1, 2007), pp. 1-55, XP055197066, Retrieved from the Internet: URL: http://japan.mt.com/jp/ja/home/supportive_content/tips_and_tricks/Guide_pH_meas/jcrcontent/downloadfile/file.res/51300047_pH-Guide_E.pdf. [retrieved on Jun. 19, 2015].

\* cited by examiner

PROCESS FOR THE SYNTHESIS OF HIGHLY PURE CATIONIC SURFACTANT PRODUCTS

FIELD OF THE INVENTION

The present invention relates to a process of preparation of cationic surfactants. Particularly the invention relates to processes for synthesis of N-fatty acyl substituted amino acid ethyl esters and their organic and inorganic acid salts thereof.

BACKGROUND OF THE INVENTION

Cationic surfactants used as antimicrobial agent is gaining increasing acceptance recently. One such antimicrobial is $N^\alpha$-Lauroyl-L-arginine ethyl ester monohydrochloride (LAE). This antimicrobial, LAE, is approved as a food ingredient in the United States [1] and a few other countries. It is also an approved compound for the cosmetic industry and hair conditioners [2]. Such acceptance of this ingredient reflects on its safety profile. Yet the product remains encumbered by impurities that reflect negatively upon its antimicrobial properties and its applications in some areas.

The prior art patents [3-8] describe the preparation of cationic surfactant compounds. US20110077423 and US20100152480 review earlier patent literature and advances the process chemistry by condensing acid halide of fatty acid with amino acid ester derivative in aqueous medium while controlling temperature and pH by eliminating use of expensive coupling agent dicyclohexylcarbodiimide (DCC) and anhydrous reaction conditions. The process described in these patents, though an advancement above the prior art, is encumbered with generation of undesirable impurities. Further, the process requires both temperature and pH control in narrow ranges. Though a comparatively pure product is claimed but the impurity profile remains the same. The described process has inherent drawback of forming undesirable impurities due to use of hydrolytic aqueous condition and harsh neutralizing base (at the concentration of sodium hydroxide being used) which at initial contact affords high unintended localized pH.

The products flowing out of the prior art processes contain several impurities. These impurities, though not desirable, were recognized in earlier specifications of the product. Following is typical impurity profile reported [9].

| | PURITY |
|---|---|
| Total ash (Vol. 4) | Not more than 2% (700°) |
| Water (Vol. 4) | Not more than 5%. Determine by the methods described in Volume 4 under "General Methods, Water Determination (Karl Fischer Method)". |
| Nα-Lauroyl-L-arginine | Not more than 3% |
| Lauric acid | Not more than 5% |
| Ethyl laurate | Not more than 3% |
| L-Arginine•HCl | Not more than 1% |
| Ethyl arginate•2HCl | Not more than 1% |

Recently better yield of 98% w/w has been reported in US20110077423. This percentage yield is presumed to be with respect to the input weight of 47.1 gm of L-arginine ethyl ester dihydrochloride (in Example 1 of the referred patent) which when converted to the theoretical yield from the reaction calculates to ~64% on molar basis. Further, the described workup of the reaction mass indicating 98% w/w yield (64% molar basis) is inclusive of the unavoidable impurities due to the inherent process conditions. Hence, for a novice in this art the improved yield numbers have to be viewed with caution as they are w/w and inclusive of the impurities formed in the reaction conditions. Thus the yield of the product reported in the prior art is low compared to the yield reported by the inventors on molar basis.

SUMMARY OF THE INVENTION

The present invention claims a process for obtaining high yield and high purity N-acyl substituted amino acid ester, its organic or inorganic salt, comprising a non-hydrolytic or nearly non-hydrolytic reaction medium involving mono or biphasic reaction system with fatty acid halide wherein the fatty acid is selected from $C_4$ to $C_{20}$ and wherein the pH is between about 7.5 to about 8.5 and the said process having no pH hot spots.

In one aspect, the process is monophasic or biphasic reaction involving solvents, organic bases or mild inorganic bases.

The organic base in the process is selected from the group consisting of triethylamine, diethylamine, diisopropylamine, pyridine, pyrolidine and piperidine and is used in molar ratio to neutralize ester of amino acid, its inorganic salts or its organic salts when reaction is carried out in organic solvent.

The mild inorganic base is selected from the group consisting of ammonium bicarbonate, ammonium carbonate, ammonium hydrogen sulfate, ammonium sulfate, sodium carbonate, sodium bicarbonate, potassium carbonate, potassium bicarbonate, ammonia gas and aqueous ammonia and wherein the mild inorganic base is used in molar ratio to neutralize ester of amino acid, its inorganic salts or its organic salts when reaction is carried out in mono or biphasic supersaturated aqueous non-hydrolytic or nearly non-hydrolytic reaction conditions. It is also envisaged that the salt used for saturation is a by-product of the reaction itself or a non-interactive salt.

In yet another aspect, the invention provides a process of obtaining high yield and high purity N-acyl substituted amino acid ester comprising the steps of:
(i) slurrying ester of amino acid or its salt and acid halide or organic base in an organic solvent at standard temperature and pressure (STP);
(ii) addition of molar ratio of organic base or acid halide at a temperature range of about 10° C. to 100° C., more preferably at a temperature range of about 20° C. to 35° C.;
(iii) acidification to obtain a soluble product and insoluble by-product
(iv) filtration of the by-product;
(v) crystallization of the product from the organic solvent; and
(vi) isolation and drying of the product.

In another aspect, the invention provides a process of obtaining high yield and high purity N-acyl substituted amino acid ester comprising the steps of:
(i) adding acid chloride to a heterogenous mixture of ester of amino acid or its salt in a supersaturated non-hydrolytic salt solution of mild inorganic base at a temperature range of 10° C. to 90° C., more preferably at a temperature range of 20° C. to 35° C.;
(ii) addition of a solvent to extract the product at a higher temperature;
(iii) separation of organic phase, filtration and crystallization of the product from the acid.

(iv) separation of the product obtained by the process of crystallization and dry to obtain high purity finished product.

In the above said process, the N-acylation is carried out by adding acid chloride to a co-solvent selected from the group consisting of THF, dioxane, ether, DME, t-butyl methyl ether, alkyl acetate and hexane and covering the supersaturated non-hydrolytic or nearly non-hydrolytic salt solution and wherein the product is retained in the co-solvent.

DESCRIPTION OF THE INVENTION

Inventors of the current applicants have focused on the process to improve the quality, which is of utmost importance to the consumer industries such as food and cosmetics. In addition, the current process not only improves the yield but is also environmental friendly as it reduces pollution.

Inventors of the current process hypothesized that the prior art product yield and quality suffers because of the hydrolysis in the aqueous media resorted to for the reaction. This can be avoided if the hydrolytic nature of the aqueous media was to be non-hydrolytic. Thus the applicants of the present invention use organic solvent as a remedy against formation of impurities.

Brine (common salt) or saturated salt solutions are indeed non-hydrolytic in nature [10] although it is not a common knowledge. In the past, the applicants have used this principle of the saturated salt solutions for the disposal of sodium metal waste. Instead of an explosive situation due to the addition of sodium metal to the so called aqueous media, in reality when saturated with salt there is no free water available for violent reaction resulting in distinctly different properties.

Halpern et al [11] have demonstrated that at lower sodium hydroxide concentration more water molecules are available for concurrent transfer with the hydroxide ion into the organic phase. Employment of 50% NaOH solution or powder NaOH affords a lower reaction rate than expected which is due to relative shortage of available water molecules.

Prior arts US20110077423 and US20100152480 have used aqueous sodium hydroxide as a base for the neutralization of L-Arginine ethyl ester dihydrochloride dissolved in water. They have preferably used 20% sodium hydroxide solution, equivalent to ~5 molar solution of NaOH, for neutralization. Mehta et al [12] in their publication on 'pH facts', have shown that the pH of 1.0 molar sodium hydroxide is 14.0 at 25° C. and it increases to the pH of 15.0 as the temperature is lowered to 0° C. This negates preference of lower temperature for neutralization due to the increased potential of hydrolysis as selected and used by the prior art. When 20% sodium hydroxide solution is added to arginine ethyl ester dihydrochloride in water, very high localized pH at the point of contact causes formation of one of the impurities (L-Arginine) because of hydrolysis of ester. Inventors of the present invention have taken caution of this impurity formation and overcome the same by use of moderate uniform alkaline condition.

US20110077423 and US20100152480, while condensing the solution by addition of lauroyl chloride and sodium hydroxide at a temperature of about 5 to 10° C. for about 3 hrs suffers from the same reaction chemistry as described above which results in the formation of impurities of $N^{\alpha}$-lauroyl-L-arginine, Lauric acid, Ethyl laurate, L-Arginine, and Ethyl arginate. Free amino acids are converted to their hydrochloride salt during isolation process.

Further to the above prior art discussion, it should be mentioned that the prior art emphasizes the need of strict pH control during the course of reaction through careful addition of sodium hydroxide solution and simultaneous addition of lauroyl chloride under continuous observation of the reaction mass pH. Though the overall reaction mass may show a controlled pH but, in fact, there will be a very high localized pH at the point of contact where sodium hydroxide solution is introduced. This again results in the formation of the impurities. Considerable reduction of impurities achieved through moderate uniform alkaline condition is further boosted by non-hydrolytic medium as envisaged by the present invention. Furthermore, non-hydrolytic medium improves yield of the crude product to near quantitative.

Further, the prior art requires temperature control in the narrow range of 5 to 10° C. during the course of reaction.

Inventor's choice of saturated salt solutions (Brine) or organic solvents in place of aqueous media overcomes the drawbacks of the prior art as described above. Further, the combination of mild bases and non-hydrolytic medium i.e. saturated salt solutions or organic solvents, do not require on-line pH control. The inventors have successfully used this very principle of lack of availability of free water during the synthesis that allows working at ambient temperature without need for any temperature control in the endothermic or exothermic part of the reaction. Free water (hydrolytic medium) favors impurity formation with respect to temperature increase.

Every aqueous saturated salt solution does not create a non-hydrolytic media. As a general rule, water insoluble salts or low solubility salts do not provide a total non-hydrolytic condition. Choice of salts such as NaCl, 8 to 15 molar NaOH, $(NH_4)_2SO_4$, KCl, LiCl, $MgCl_2.6H_2O$, $CaCl_2.2H_2O$, $Na_2CO_3$, $CdCl_2.2.5H_2O$, and $BaBr_2.2H_2O$ etc. are used to create saturated aqueous solution providing non-hydrolytic mixture or a sufficiently non-hydrolytic mixture [10]. However, the suitability of the salt also has to be in step with the interactions it may have with the reaction on hand. The salt used for saturation may also be the byproduct of reaction itself or any other non-interactive salt chosen based on the reaction under consideration.

Following sequence of reaction steps is illustrative of the technique but not limited to the combinations used as an example:

Take 300 ml 5% to 10% common salt solution in a 3 liter round bottom flask at room temperature (RT).

Add 112 gm L-Arginine ethyl ester dihydrochloride in one lot to the common salt solution under stirring.

100 gram of mild Base, sodium bicarbonate is added in portions in 2 hrs.

1200 ml of solvent tetrahydrofuran (THF) is added to furnish two phase reaction system.

Add solution of 88 ml Lauroyl Chloride in 150 ml Solvent THF in 3 hrs.

After addition is over, the reaction mixture is, monitored by HPLC/TLC and stirred until completion.

Cool the mixture to 20-25° C. under constant stirring and adjust pH by adding, as per required salt, organic acid or inorganic acid (acetic acid, formic acid, maleic acid, fumaric acid, propionic acid, hydrochloric acid, hydrobromic acid or hydroiodic acid etc.)

Separate the organic layer and wash it with saturated brine followed by drying the organic layer over anhydrous sodium sulfate.

Filter the organic layer and crystallize the product.

Isolate and dry crystallized product

Isolated product is over 94% molar yield with purity over greater than 99.5% N-Acylation of ester of amino acid and its inorganic salts or its organic salts of the invention includes but not limited to ester of amino acid or hydrochloride of ester of amino acid or sulfate of ester of amino acid or acetate of ester of amino acid.

The example above should in no way be construed as restrictive of the science detailed.

Working Procedure

Biphasic system—Biphasic system arises in case of non-hydrolytic aqueous medium as described above.

Monophasic system—

Non-hydrolytic aqueous medium: In the case of monophasic system, organic solvent is not added from the beginning (like 1200 ml of THF above). N-Acylation reaction is carried out by addition of the fatty acid halide, selected from $C_4$-$C_{20}$, directly to the non-hydrolytic medium. The product falls out of the medium and filtered and crystallized after acidification. Alternatively product is extracted in suitable organic solvent after acidification of the reaction mixture and crystallized.

A variation of the above is by the addition of a co-solvent selected from the group consisting of THF, dioxane, ether, DME, t-butyl methyl ether, alkyl acetate and hexane and covering the super saturated non-hydrolytic or nearly non-hydrolytic salt solution and adding therein acid chloride for the N-acylation and retaining the generated product in the co-solvent.

Organic medium: In the case of organic solvent as medium, same solvent is used as a carrier for the fatty acid halide. After the completion of the reaction it is acidified to obtain the product. Combination of reaction medium solvent and the neutralizing organic base will decide if the byproduct is soluble or insoluble in the reaction solvent. In case of soluble byproduct (organic base acid salt) reaction mixture is washed with water and product is isolated and crystallized from organic solvent and dried. When the byproduct (organic base acid salt) is insoluble it is filtered off and product is isolated and crystallized.

The use of non-hydrolytic or nearly non-hydrolytic reaction mass is the governing principle in obtaining high quality product with high yield in combination with pH not exceeding moderate levels (between about 7.5 to about 8.5) in general and specifically having no pH hot spots in the process. The process described allows for numerous permutations and combinations for the use of solvents, organic bases, mild inorganic bases in mono and/or biphasic and/or heterogeneous, organic and aqueous system which should be appreciated by a person skilled in the art.

It is also noted that salts of weak bases and strong acids have cations which behave as acids in aqueous solution, and so will give rise to solutions with pH values less than 7. The ions from which the salts of strong acids and strong bases are constituted do not react with water, and so do not disturb the neutrality of their aqueous solution.

Examples of these variations are given below which are merely illustrative should in no way be construed as limiting.

Definitions

The application provides certain terminologies which are explained here but are to be given the broadest scope.

By pH hot spot it means localized extreme pH condition in otherwise a moderate pH environment. The pH extreme can be acidic or alkaline.

By non-hydrolytic or nearly non-hydrolytic, it is meant that the reaction is in the absence of availability of free water molecule.

By 'high yield' it is meant that the product yielded by the process of the invention is at least 92% and preferably between 92-97%.

By 'high purity' it is meant that the purity of the product yielded by the process of the invention is at least 99%.

The organic bases of the invention includes but not restricted to triethylamine, diethylamine, diisopropylamine, pyridine, pyrolidine and piperidine.

The mild inorganic bases of the invention includes but not restricted to ammonium bicarbonate, ammonium carbonate, ammonium hydrogen sulfate, ammonium sulfate, sodium carbonate, sodium bicarbonate, potassium carbonate, potassium bicarbonate, ammonia (gas) and aqueous ammonia

EXAMPLES

Example 1

L-Arginine ethyl ester dihydrochloride (27.5 grams, 0.1 mole) is slurried in 500 mL of chloroform while stirring, triethyl amine (20.2 grams, equivalent to 0.2 mole) is added dropwise and stirred for 30 mins, followed by dropwise addition of lauroyl chloride (22 grams, 0.1 mole) at room temperature, reaction being slightly exothermic, 5° C. rise in temperature was observed. Reaction mixture is stirred for 2 hours at room temperature, triethyl amine (10.1 grams, 0.1 mole) is added during 20 minutes and is refluxed until completion of the reaction (monitored by HPLC/TLC). Triethylamine hydrochloride salt is quite soluble in chloroform.

Chloroform is distilled off to obtain 93 grams of crude containing triethylamine hydrochloride salt along with product. It is dissolved in 250 mL water, cooled to 10° C., acidified by adding 10% hydrochloric acid to obtain specific acidic pH. Product was extracted in Ethyl Acetate (250 mL) while stirring biphasic system at temperature higher then room temperature. Aqueous phase is separated, organic phase is washed with 50% brine solution (25 mL), dried over anhydrous sodium sulfate. Filtration and crystallization of solvent furnishes 38 grams of lauroyl ethyl arginate hydrochloride (90.26% yield) of purity >99%.

Example 2

L-Arginine ethyl ester dihydrochloride (27.5 grams, 0.1 mole) is slurried in 100 mL of Tetrahydrofuran while stirring, triethyl amine (20.2 grams, equivalent to 0.2 mole) is added dropwise and stirred for 30 mins, followed by dropwise addition of lauroyl chloride (22 grams, 0.1 mole) at 15° C., stirred at room temperature for 2 hours followed by addition of triethyl amine (10.1 grams, 0.1 mole). Reaction mixture is stirred at 40° C. until completion of the reaction (monitored by HPLC/TLC).

Insoluble salt of triethylamine hydrochloride (30 grams) is filtered off, and solvent is evaporated to furnish 65 grams of crude product. Isolation followed as explained in Example 1 furnishes 39.6 grams of Lauroyl ethyl arginate hydrochloride (94.06% yield) of purity >99%.

Example 3

L-Arginine ethyl ester dihydrochloride (55.0 grams, 0.2 mole) is slurried in 150 mL of 5% brine solution while stirring, sodium bi carbonate (50.40 grams, equivalent to 0.6 mole) is added in portions during 2 hours and stirred until no effervescence. To the highly saturated turbid solution, is added dropwise lauroyl chloride (44.00 grams, 0.2 mole) maintaining room temperature during 2 hours. Reaction mixture is stirred at 35° C. until completion of the reaction (monitored by HPLC/TLC). Reaction mixture is cooled while stirring at 5 to 10° C., acidified by adding 10% HCl till pH=3, stirred at the same temperature to allow crystallization, filtration and drying furnishes 78 grams of Lauroyl ethyl arginate hydrochloride (92.85% yield) of high purity.

Example 4

L-Arginine ethyl ester dihydrochloride (112.0 grams, 0.4 mole) is slurried in 300 mL of 5% brine solution while stirring, sodium bi carbonate (100.8 grams, equivalent to 1.2 mole) is added in portions during 2.5 hours and stirred until no effervescence. To the highly saturated turbid solution, is added 500 mL of tetrahydrofuran followed by dropwise addition of lauroyl chloride solution (88.00 grams, 0.4 mole in 150 mL THF) maintaining room temperature during 3 hours. Reaction mixture is stirred at 35° C. until completion of the reaction (monitored by HPLC/TLC). Reaction mixture is cooled while stirring at 5 to 10° C., acidified by adding 10% HCl solution till pH=3, and aqueous phase is separated, product is very soluble in THF at room temperatue, organic layer was dried over anhydrous sodium sulfate, crystallized at 0° C. for 4 hours after filtration and drying furnishes 158.4 grams of Lauroyl ethyl arginate hydrochloride (94.06% yield) of high purity.

REFERENCES

1. Bakal G, Diaz A: The Lowdown on Lauric Arginate. *Food Quality magazine*, 2005.
2. Barroso J M: Directive 76/768/EEC concerning cosmetic products. *Official Journal of the European Union* 2010.
3. INFANTE MARTINEZ-PARDO M R, CONTIJOCH MESTRES A, ERRA SERRABASA P: PROCESS FOR THE SYNTHESIS OF CATIONIC SURFACTANTS OBTAINED FROM THE CONDENSATION OF FATTY ACIDS WITH ESTERIFIED DIBASIC AMINOACIDS. EP 0 749 960 B1 2001
4. CONTIJOCH MESTRES A, RODRIGUEZ MARTINEZ F J, SEGUER BONAVENTURA J: PROCESS FOR THE PREPARATION OF CATIONIC SURFACTANTS. EP 1 294 678 B1 2006.
5. Yoshida R, Shishido T: Process for preparing N-higher aliphatic acyl derivatives of amino acids, peptides or Proteins. U.S. Pat. No. 3,985,722 1976.
6. Martinez-Pardo M R I, Mestres A C, Serrabasa P E: Process for the synthesis of cationic surfactants comprising esterification with basic Character Amino Acid U.S. Pat. No. 5,780,658 1998.
7. Ghare V S: PROCESS FOR SYNTHESIS OF CATIONIC SURFACTANTS. US 2010/0152480 A1 2010.
8. Ghare V S: PROCESS FOR THE SYNTHESIS OF HYDROCHLORIDE SALT OF N-FATTY ACYLSUBSTITUTED AMINO ACID ETHYL ESTERS. US 2011/0077423 A1 2011.
9. JECFA: ETHYL LAUROYL ARGINATE *FAO JECFA Monographs* 7 (2009).
10. Lakshmanan A R, Prasad M V R, Ponraju D, Krishnan H: A novel method of non-violent dissolution of sodium metal in a concentrated aqueous solution of Epsom salt. *Journal of Solid State Chemistry* 2004, 177(10):3460-3468.
11. Halpern M: Hydroxide ion initiated reactions under phase-transfer-catalysis conditions. 5. Isomerization of allylbenzene via hydroxide ion extraction. *The Journal of Organic Chemistry* 1983, 48(7):1022-1025.
12. Mehta D, Mehta P: pH Facts & Fallacies. *Chemical Industry Digest* 2006:53-57.

We claim:

1. A process for obtaining high yield and high purity N-acyl substituted amino acid ester, its organic or inorganic salt, comprising:
   reacting an L-arginine ethyl ester or salt thereof with a C4 to C20 fatty acid halide in a reaction medium having no availability of free water molecules, involving a monophasic or biphasic reaction system comprising a mild inorganic base, wherein the pH is between about 7.5 to about 8.5 and has no pH hot spots; and
   isolating the resulting N-acylated L-arginine ethyl ester, wherein the purity is >99% and the yield is >92%,
   wherein the mild inorganic base is selected from the group consisting of ammonium hydrogen sulfate, ammonium sulfate, ammonia gas and aqueous ammonia, and wherein the mild inorganic base is used in molar ratio to neutralize ester of amino acid, its inorganic salts or its organic salts when reaction is carried out in mono or biphasic supersaturated aqueous non-hydrolytic or nearly non-hydrolytic reaction condition.

2. The process of claim 1, wherein a salt used for the reaction condition is a by-product of the reaction itself or a non-interactive salt.

* * * * *